(12) United States Patent
Herzog et al.

(10) Patent No.: US 12,102,294 B2
(45) Date of Patent: Oct. 1, 2024

(54) METHOD FOR PRODUCING A MEDICAL INSTRUMENT

(71) Applicant: RICHARD WOLF GMBH, Knittlingen (DE)

(72) Inventors: Frank Herzog, Lichtenfels (DE); Thomas Thyroff, Michelau (DE); Frank Wehrheim, Bretten (DE); Markus Lienhart, Ottersweier (DE); Artur Reiswich, Gondelsheim (DE)

(73) Assignee: RICHARD WOLF GMBH, Knittlingen (DE)

( * ) Notice: Subject to any disclaimer, the term of this patent is extended or adjusted under 35 U.S.C. 154(b) by 743 days.

(21) Appl. No.: 16/489,206

(22) PCT Filed: Feb. 9, 2018

(86) PCT No.: PCT/EP2018/053256
§ 371 (c)(1),
(2) Date: Jan. 8, 2020

(87) PCT Pub. No.: WO2018/158062
PCT Pub. Date: Sep. 7, 2018

(65) Prior Publication Data
US 2020/0113698 A1    Apr. 16, 2020

(30) Foreign Application Priority Data
Feb. 28, 2017 (DE) .................... 10 2017 104 188.5

(51) Int. Cl.
*A61B 1/012* (2006.01)
*A61B 1/00* (2006.01)
(Continued)

(52) U.S. Cl.
CPC ............... *A61B 1/012* (2013.01); *A61B 1/00* (2013.01); *A61F 2/3094* (2013.01);
(Continued)

(58) Field of Classification Search
CPC .......................................... A61B 1/012–1/018
See application file for complete search history.

(56) References Cited

U.S. PATENT DOCUMENTS 10,464,133 B2   11/2019  Danger et al.
10,539,255 B2 *  1/2020  Kroll ....................... B22F 5/10
(Continued)

FOREIGN PATENT DOCUMENTS

CN    105881185 A    8/2016
CN    106392893 A    2/2017
(Continued)

OTHER PUBLICATIONS

PCT International Search Report Corresponding to Application No. PCT/EP2018/053256 on May 25, 2018.

*Primary Examiner* — Jacob J Cigna
(74) *Attorney, Agent, or Firm* — Dority & Manning, P.A.

(57) ABSTRACT

Methods of manufacturing a medical component include additively manufacturing a medical component at least in part by successive, layer-by-layer, selective exposure and associated successive, layer-by-layer, selective solidification of construction material layers made of a construction material solidifiable with an energy beam. The medical component is insertable at least partially into a body of a living being, and the medical component includes a channel structure that has a tubular channel through which a medium and/or at least one functional element can be passed.

19 Claims, 4 Drawing Sheets

Figure 1:
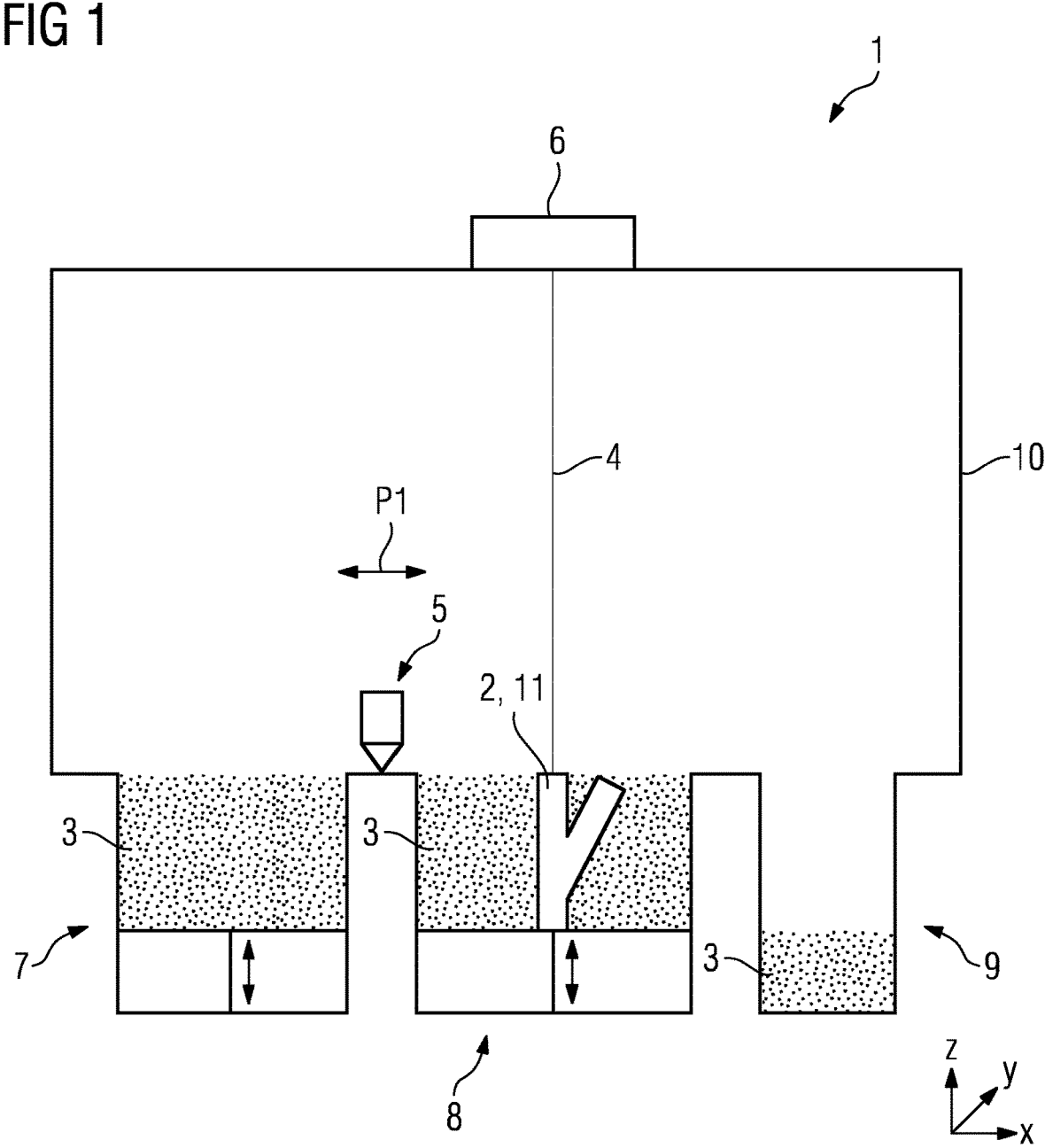

(51) Int. Cl.
*A61F 2/30* (2006.01)
*A61M 25/00* (2006.01)
*B22F 10/28* (2021.01)
*B22F 10/66* (2021.01)
*B33Y 10/00* (2015.01)
*B33Y 30/00* (2015.01)
*B33Y 70/00* (2020.01)
*B33Y 80/00* (2015.01)

(52) U.S. Cl.
CPC ......... *A61M 25/0021* (2013.01); *B22F 10/28* (2021.01); *B22F 10/66* (2021.01); *A61F 2002/30968* (2013.01); *A61F 2240/002* (2013.01); *A61M 2207/00* (2013.01); *B33Y 10/00* (2014.12); *B33Y 30/00* (2014.12); *B33Y 70/00* (2014.12); *B33Y 80/00* (2014.12)

(56) References Cited

U.S. PATENT DOCUMENTS

| | | | |
|---|---|---|---|
| 10,624,530 B2 * | 4/2020 | Graham | A61B 1/0055 |
| 10,668,252 B2 | 6/2020 | White et al. | |
| 2003/0050622 A1 | 3/2003 | Humes et al. | |
| 2015/0173593 A1 * | 6/2015 | Han | A61B 1/07 |
| | | | 600/137 |
| 2016/0051385 A1 | 2/2016 | Hollister et al. | |
| 2016/0166284 A1 | 6/2016 | Hacking et al. | |
| 2016/0271379 A1 | 9/2016 | Pouliot | |
| 2017/0027606 A1 * | 2/2017 | Cappelleri | A61B 17/29 |
| 2017/0340430 A1 | 11/2017 | Moore | |
| 2020/0029822 A1 * | 1/2020 | Morris | A61B 17/0218 |

FOREIGN PATENT DOCUMENTS

| | | | | |
|---|---|---|---|---|
| DE | 102012000466 B3 | | 4/2013 | |
| DE | 102015204486 A1 | * | 9/2016 | ............. A61B 17/29 |
| DE | 102016119707 A1 | * | 4/2018 | ......... A61B 1/00128 |
| EP | 3034041 A1 | | 6/2016 | |
| WO | WO2011/026164 A1 | | 3/2011 | |
| WO | WO2013/137283 A1 | | 9/2013 | |
| WO | WO2016/083784 A1 | | 6/2016 | |
| WO | WO2018/158062 A1 | | 9/2018 | |

* cited by examiner

METHOD FOR PRODUCING A MEDICAL INSTRUMENT

DESCRIPTION

The invention relates to a method for manufacturing a medical component insertable, at least in segments, into a body of an object, in particular of a living being, comprising a channel structure including at least one, in particular tubular, channel, through which a medium and/or at least one functional element can be passed.

Medical components insertable into a body of an object, in particular of a living being, which comprise a channel structure including at least one, in particular tubular, channel, are basically known. Such medical components are utilized, for example, in the field of minimally invasive surgery, in which medical media, i.e., for example, rinsing liquids, or functional elements, such as instruments for manipulating, i.e., for example, removing or sampling, tissue, and/or instruments for examining tissue, are passed through the channel or channels of a particular component-side channel structure. For example, an endoscope typically comprises such a medical component, through the channel structure of which certain medical media or functional elements can be passed.

Such medical components have typically been manufactured so far from individual tube or hose segments, i.e., in particular by connecting individual tube or hose segments. The manufacture of such medical components is often complex due to the small dimensions, in particular of the channel structure. The cost increases with the degree of complexity of the geometric-structural shape of the particular channel structure or of the medical components in general; for example, medical components comprising a channel structure including multiple, if necessary, branched, channels communicating with one another can be manufactured in satisfactory quality only with an extremely great amount of effort.

The problem addressed by the invention is therefore that of providing a method for manufacturing such medical components, which is improved by comparison.

The method described herein is utilized for manufacturing a medical component ("component") insertable, at least in segments, into an object, i.e., in particular into a human being or an animal. The component, which typically has an elongate geometric-structural shape, comprises a channel structure, which is also to be referred to as or considered to be a hollow structure, and which includes at least one, typically elongate, channel, which is also to be referred to as or considered to be a cavity. A particular channel typically extends between component-side openings arranged or formed, in particular, in the area of particular free ends of the component; a first component-side opening is typically located within an object during the operation of the component, and a second component-side opening is typically located outside the object during the operation of the component. The channel structure can comprise multiple channels, as becomes apparent in the following.

The component can be utilized in the field of minimally invasive surgery, in which gaseous or liquid media, i.e., for example, rinsing liquids, or medical functional elements, such as instruments for manipulating, i.e., for example, removing or sampling, tissue, and/or instruments for examining tissue, are passed through the channel or channels of the component-side channel structure. Specifically, the component can form, for example, an endoscope or a component of an endoscope.

The component is manufactured, at least in segments, in particular completely, using a powder-based, additive manufacturing method, i.e., with the aid of successive, layer-by-layer, selective exposure and associated successive, layer-by-layer, selective solidification of construction material layers made of a construction material solidifiable with the aid of an energy beam. The construction material is typically present in powdered form, i.e., in the form of a powder. For example, a metal or a metal alloy, in particular a CoCr alloy, an iron alloy, preferably stainless steel, or a plastic, in particular a photopolymer or a thermoplastic polymer, can be utilized as the powdered construction material.

The successive, layer-by-layer, selective exposure and solidification of particular construction material layers to be solidified takes place on the basis of component-specific construction data. Such construction data describe the geometric-structural shape of the component to be additively manufactured and can include, for example, "sliced" CAD data of the component to be additively manufactured. The method can be implemented, for example, as a selective laser melting method (SLM method) or as a selective laser sintering method (SLS method).

In order to manufacture the component, a device is therefore utilized for the additive manufacturing of three-dimensional objects with the aid of successive, layer-by-layer, selective exposure and associated successive, layer-by-layer, selective solidification of construction material layers made of a powdered construction material solidifiable with the aid of an energy beam. The device can be designed, for example, as an SLM device, i.e., as a device for carrying out selective laser melting methods (SLM methods), or as an SLS device, i.e., as a device for carrying out selective laser sintering methods (SLS methods).

The additive manufacturing of particular components offers numerous manufacturing-related advantages: In principle, any channel (cross section) geometries or channel structure (cross section) geometries can be manufactured, i.e., the geometric-structural design freedom of the channels or of the channel structures of the components is nearly unlimited. For example, in particular (acute-) angled, transitions between channels formed by branches or junctions of channels can be manufactured in a simplified way. Undercuts, gaps, and abutment points can be improved; in principle, a reduction of the number of undercuts, gaps, and abutment points is also possible. Moreover, a considerable reduction of the working steps for manufacturing particular components is possible, which positively affects the cost-effectiveness of the manufacture of particular components.

The additive manufacturing of particular components also offers numerous structural advantages: For example, the additively manufactured components are distinguished by particular structural, in particular mechanical, as well as hygienic properties. The components can be formed in a highly integrated manner with respect to function; consequently, highly functional components can be formed.

Overall, an improved method for manufacturing such components is therefore available.

A particular channel can be designed extending in a straight line at least in segments, if necessary completely, and/or extending in a curved manner at least in sections, if necessary completely. A particular channel can therefore have been designed extending in a straight line at least in segments, if necessary completely, and/or extending in a curve manner at least in sections, if necessary completely. As mentioned, the component and, therefore, the channels as well, typically have an elongate geometric-structural shape, and so a particular channel can comprise channel sections extending differently along its longitudinal extension, i.e., channel sections extending in a straight line, on the one hand, and channel sections extending in a curved manner, on the other hand.

A particular channel can be designed, in particular in the area of a free end of the component, comprising at least one branch point at which the channel branches into at least two channels (secondary channels). A particular channel can therefore have been designed, in particular in the area of a free end of the component, including at least one branch point, at which the channel branches into at least two channels. Of course, such second channels resulting from a branching of a first channel can also be designed including such branch points at which each of the second channels branches into at least two further channels. The component can therefore comprise a different number of channels along its longitudinal extension; the number of channels upstream and downstream from such a branch point can therefore vary due to such branchings of at least one channel into at least two channels. Such a branching of a channel can be, for example, advantageous for a certain delivery or distribution of a medium, which is flowing through the channel structure out of the component, i.e., it can be generally advantageous for the functionality of the component.

A particular channel can be designed, in particular in an area located between two free ends of the component, comprising at least one junction at which a channel branches into at least one further channel (side channel). A particular channel can therefore have been designed, in particular in an area located between two free ends of the component, to comprise at least one junction at which a channel branches into at least one further channel. Of course, such second channels resulting from a branching of a first channel can also be designed including such junctions at which each of these second channels branches into at least one further channel. In this way as well, the component can comprise a different number of channels along its longitudinal extension; the number of channels upstream and downstream from such a junction can therefore vary due to such a branching of a channel into at least two channels. Such a branching of a channel can be, for example, advantageous for the insertion of a medical functional element, i.e., for example, a medical instrument, via a first channel and the simultaneous supply of a medium via a branched second channel, i.e., it can be generally advantageous for the functionality of the component.

With respect to its geometric-structural dimensions, it is the case, in particular, that a particular channel or a channel section forming a component of a particular channel can be designed having an inner diameter of the channel in a range between 0.25 mm and 3 mm, in particular in a range between 0.5 mm and 2.5 mm (exceptions in the upward and downward directions are conceivable). It is possible, of course, that a particular channel has different inner diameters along the longitudinal extension of the channel. The wall thickness of the walls delimiting a particular channel can also be in a range between 0.25 mm and 3 mm, in particular in a range between 0.5 mm and 2.5 mm (exceptions in the upward and downward directions are conceivable). It is possible, of course, that the walls delimiting a particular channel have different wall thicknesses along the longitudinal extension of the channel.

On the basis of embodiments presented above, it is apparent that the component-side channel structure can comprise multiple channels. The channel structure can be designed comprising multiple channels communicating with one another, in particular at appropriate branch points or junctions, or comprising multiple channels that are not communicating with one another. The channel structure can therefore have been designed comprising multiple channels communicating with one another, in particular at appropriate branch points or junctions, or comprising multiple channels that are not communicating with one another.

The channels can be designed or can have been designed, for example, to be coaxially arranged. Therefore, the channel structure, viewed in cross section, can comprise multiple channels extending coaxially, i.e., extending within one another. A first or inner channel having a first diameter can extend within a second or outer channel having a larger second outer diameter. As a result, it is possible to implement different functionalities of the channel structure across the overall cross section of the component; for example, a medical functional element, i.e., for example, a medical instrument, can be passed through an inner channel, and a medium can be passed through an outer channel enclosing the inner channel, or vice versa. It is also conceivable, of course, to pass different media, if necessary having different flow parameters, or different functional elements, through different channels. In particular, it is conceivable to utilize a first channel as a supply channel for supplying a medium and to utilize a second channel as a drainage channel for draining a medium.

Alternatively or additionally to a coaxial arrangement of multiple channels, multiple channels can also be designed or can have also been designed to be arranged spaced apart or adjacent to one another, circumferentially about a central axis of the component. In this way as well, it is possible to implement different functionalities of the channel structure across the overall cross section of the component; for example, a medical functional element, i.e., for example, a medical instrument, can be passed through a first channel, and a medium can be passed through a second channel arranged circumferentially adjacent to the first channel. It is also conceivable, of course, to pass different media, if necessary having different flow parameters, or different functional elements through different channels.

Within the scope of the method, i.e., in particular after completion of the additive construction process of the component, at least one measure can be carried out for mechanically processing, at least in segments, the walls of the component or its surface delimiting a particular channel. Due to an appropriate mechanical processing or reworking, the structural properties, in particular of the surfaces, of the walls delimiting the particular channel can be affected in a targeted manner in order to affect, for example, the flow behavior of a medium flowing through the particular channel, for example, by forming a certain surface structure or a certain surface roughness.

As a measure for mechanically processing, at least in segments, the wall thickness of the walls of the component delimiting a particular channel, a fluid flow, which contains, in particular abrasive, particles removing material from the walls delimiting the at least one channel, can be passed through a particular channel. By passing a fluid flow containing material-removing particles through the channel, the wall thickness of the walls can be reduced to a desired dimension or the channel cross section can be increased to a desired dimension. For example, hard mineral particles (or mixtures thereof), i.e., in particular, corundum particles (or mixtures thereof), can be utilized as material-removing particles. The fluid flow can be a gas or liquid flow, i.e., for example, an air or water flow, which flows through the particular channel at a flow rate sufficiently high for removing material from the walls with the aid of the particles.

As a measure for mechanically processing, at least in segments, the surface of the walls of the component delimiting the particular channel, a fluid flow, which contains particles smoothing the surface of the walls delimiting the at least one channel, can be passed through a particular channel. By passing a fluid flow containing smoothing particles through the channel, the surface of the walls can be formed having a desired roughness. For example, hard glass or silicon oxide particles (or mixtures thereof), i.e., in particular, glass bead particles (or mixtures thereof), can be utilized as smoothing particles. The fluid flow can be, in turn, a gas or liquid flow, which flows through the particular channel at a flow rate, which is sufficiently high for smoothing the surface with the aid of the particles. After an appropriate smoothing, the surface of the walls delimiting the at least one channel can have, for example, a surface roughness Ra below 0.9, in particular below 0.8.

In any case, the fluid flow is typically directed from channel sections or channels having a comparatively larger cross-sectional area in the direction of channel sections or channels having a comparatively smaller cross-sectional area, and the angle of entry of the particular fluid flow is in a range typically between 0° and 90° in relation to the central axis of the particular channel, depending on the course of the particular channel. In this way, particularly positive removal and smoothing results can be achieved.

The component can be designed or can have been designed comprising an introduction section including an introduction opening for introducing the particular particle-containing fluid flow into the particular channel. The introduction, in particular of the particles, can therefore take place via an introduction section designed specifically for this purpose. The introduction section can form an inherent part of the component. After the at least one measure has been carried out for mechanically processing, at least in segments, the walls of the component delimiting the at least one channel, the introduction section can be removed.

At least one handling element, in particular a handle element for a user, or a tool element, in particular a grasping element, for example, for grasping tissue of an object, can be arranged or formed or can have been arranged or formed on the component, in particular in the area of a free end of the component. The handling element can be detachably (without causing damage or destruction) or non-detachably fastened on the component as a separate component group. It is also conceivable, of course, to additively manufacture the handling element, i.e., to form it as an inherent part of the component, in particular within the scope of the additive manufacturing of the component.

The component can be designed or can have been designed comprising at least one extension and/or compression structure enabling an extension or compression, in segments, of the component in the longitudinal direction of the component. Therefore, the component can be extended or compressed, in segments, in a targeted manner, which improves, for example, its handling, in particular within an object. Appropriate extension and/or compression structures can have, for example, a bellows-like or -shaped geometric-structural shape, which can be readily formed within the scope of the additive manufacturing of the component.

The component can be designed or can have been designed comprising at least one permeation structure enabling a permeation, in segments, of a medium out of a channel into the surroundings around the component. Therefore, the component may be utilized for a targeted release of a medium, i.e., for example, a medically active substance, via an appropriate permeation structure, which can be formed, for example, by permeation areas or openings, which are "passable" by a medium.

The invention further relates to a component, which comprises a channel structure including at least one, in particular tubular, channel, through which a medium and/or at least one medical functional element, in particular a tool element, can be passed. The component is distinguished by the fact that it is manufactured according to a method as described. Therefore, all comments made in conjunction with the method apply similarly for the component.

Moreover, the invention relates to a device for the additive manufacturing of three-dimensional objects with the aid of successive, layer-by-layer, selective exposure and associated successive, layer-by-layer, selective solidification of construction material layers made of a powdered construction material solidifiable with the aid of an energy beam. The device is distinguished by the fact that it is configured for carrying out the method as described, i.e., for the additive manufacturing of an appropriate component. Therefore, all comments made in conjunction with the method also apply similarly for the device.

The device can be designed, for example, as an SLM device, i.e., as a device for carrying out selective laser melting methods (SLM methods), or as an SLS device, i.e., as a device for carrying out selective laser sintering methods (SLS methods).

The device comprises functional components typically required for carrying out additive construction processes. These include, in particular, a coating unit, which is configured for forming construction material layers to be selectively solidified (in the construction plane of the device), and an exposure unit, which is configured for selectively exposing construction material layers to be selectively solidified (in the construction plane of the device). The coating unit typically comprises multiple components, i.e., for example, a coating element including an, in particular blade-shaped, coating tool, as well as a guide unit for guiding the coating element along a defined trajectory. The exposure unit also typically comprises multiple components, i.e., for example, a beam generating unit for generating an energy or laser beam, a beam deflection unit (scanner unit) for deflecting an energy or laser beam generated by the beam generating unit onto an area, to be exposed, of a construction material layer to be selectively solidified, as well as various optical elements, such as lens elements, objective elements, etc.

The invention is explained in greater detail with reference to exemplary embodiments in the figures. Wherein:

FIG. 1 shows a schematic representation of a device according to an exemplary embodiment; and FIGS. 2-9 each show a schematic representation of a medical component according to an exemplary embodiment.

FIG. 1 shows a schematic representation of a device 1 according to an exemplary embodiment. The device 1 is utilized for the additive manufacturing of three-dimensional objects 2, i.e., in particular technical components or technical component groups, with the aid of successive, layer-by-layer, selective exposure and associated successive, layer-by-layer, selective solidification of construction material layers made of a powdered construction material 3 solidifiable with the aid of an energy or laser beam 4. The device 1 can be designed as a LaserCUSING® device, i.e., as a device for carrying out selective laser melting methods.

The device 1 comprises the functional components necessary for carrying out additive construction processes; for example, a coating unit 5 and an exposure unit 6 are shown in FIG. 1. The coating unit 5 is configured for forming construction material layers, which are to be selectively exposed and selectively solidified, in a construction plane of the device 1. The coating unit 5 comprises a coater element component group (not described in greater detail) including multiple coater elements (not shown), which is mounted so as to be movable with the aid of guide unit (not shown) in the horizontal direction, as indicated by the double arrow P1. The exposure unit 6 is configured for selectively exposing construction material layers to be selectively solidified in the construction plane of the device 1 and, for this purpose, comprises a beam generating unit (not shown), which is configured for generating a laser beam 4, a beam deflection unit (not shown), if necessary, which is configured for deflecting a laser beam 4 generated by the beam generating unit onto an area, to be exposed, of a construction material layer to be selectively solidified, as well as various optical elements, such as filter elements, objective elements, lens elements, etc.

Moreover, FIG. 1 shows a metering module 7, a construction module 8, and an overflow module 9, which are docked to a lower area of an inertable process chamber 10 of the device 1. The aforementioned modules 7 through 9 can also form a lower area of the process chamber 10.

With the aid of the device 1 shown in FIG. 1, a method can be implemented for the additive manufacturing of a medical component 11 insertable, at least in segments, into an object, i.e., in particular into a human being or an animal. A particular component 11 is manufactured with the aid of successive, layer-by-layer, selective exposure and associated successive, layer-by-layer, selective solidification of construction material layers made of a construction material 3 solidifiable with the aid of an energy or laser beam 4. For example, a metal or a metal alloy, in particular a CoCr alloy, an iron alloy, preferably stainless steel, or a plastic, in particular a photopolymer or a thermoplastic polymer, can be utilized as the construction material 3. The successive, layer-by-layer, selective exposure and solidification of particular construction material layers to be selectively solidified takes place on the basis of component-specific construction data. Such construction data describe the geometric-structural shape of the component 11 to be additively manufactured and can include, for example, "sliced" CAD data of the component 11 to be additively manufactured.

A particular component 11 can be utilized in the field of minimally invasive surgery, in which gaseous or liquid media, i.e., for example, rinsing liquids, or medical functional elements, such as instruments for manipulating, i.e., for example, removing or sampling, tissue, and/or instruments for examining tissue, are passed through the channel or channels 13 of the component-side channel structure 12. Specifically, a particular component 11 can form, for example, an endoscope or a component of an endoscope.

Exemplary embodiments of such components 11 are shown in FIGS. 2 through 9. On the basis of FIGS. 2 through 9, it is apparent that the components 11 each have an elongate geometric-structural shape.

A particular component 11 comprises a channel structure 12, which includes at least one channel 13. A particular channel 13 typically extends between component-side openings 14, 15 arranged or formed, in particular, in the area of particular free ends of a particular component 11.

Figure 2:
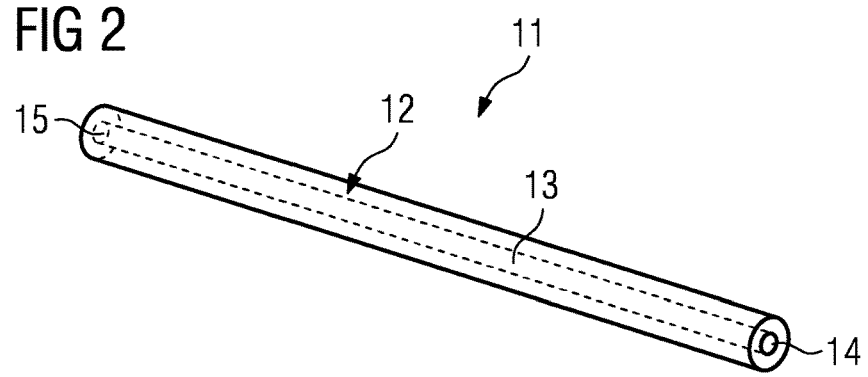
Figure 3:
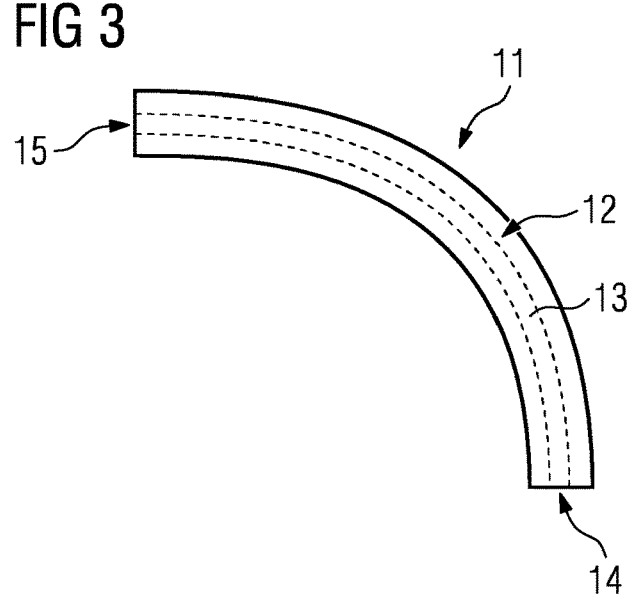

On the basis of the exemplary embodiments shown in FIGS. 2 and 3, in each of which a perspective view of a component 11 is represented, it is apparent that a particular channel 13 can be designed extending in a straight line or in a curved manner. The same applies for the entire component 11, wherein it is to be generally noted, however, that the basic shape of a particular channel 13 does not need to correspond to the basic shape of a particular component 11. Mixed forms, for example, of the exemplary embodiments shown in FIGS. 2 and 3, are also possible, of course, and so a particular channel 13 can comprise channel sections extending along its longitudinal extension in different ways, i.e., channel sections extending in a straight line, on the one hand, and channel sections extending in a curved manner, on the other hand.

Figure 4:
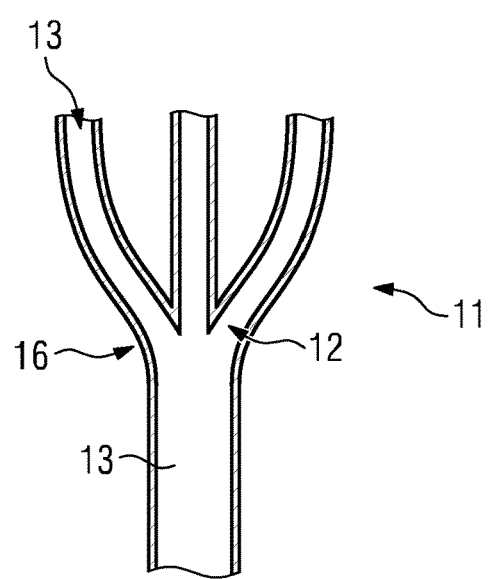

On the basis of the exemplary embodiment shown in FIG. 4, in which a longitudinally cut view of a component 11 is represented, it is apparent that a channel 13 can be designed, in the area of a free end of the component 11, comprising a branch point 16 at which the channel 13 branches off into at least two, in this case three, channels 13 (secondary channels). The component 11 therefore comprises a different number of channels 13 along its longitudinal extension; the number of channels 13 upstream and downstream from such a branch point 16 can therefore vary due to such branchings the channel 13 into at least two channels 13.

Figure 5:
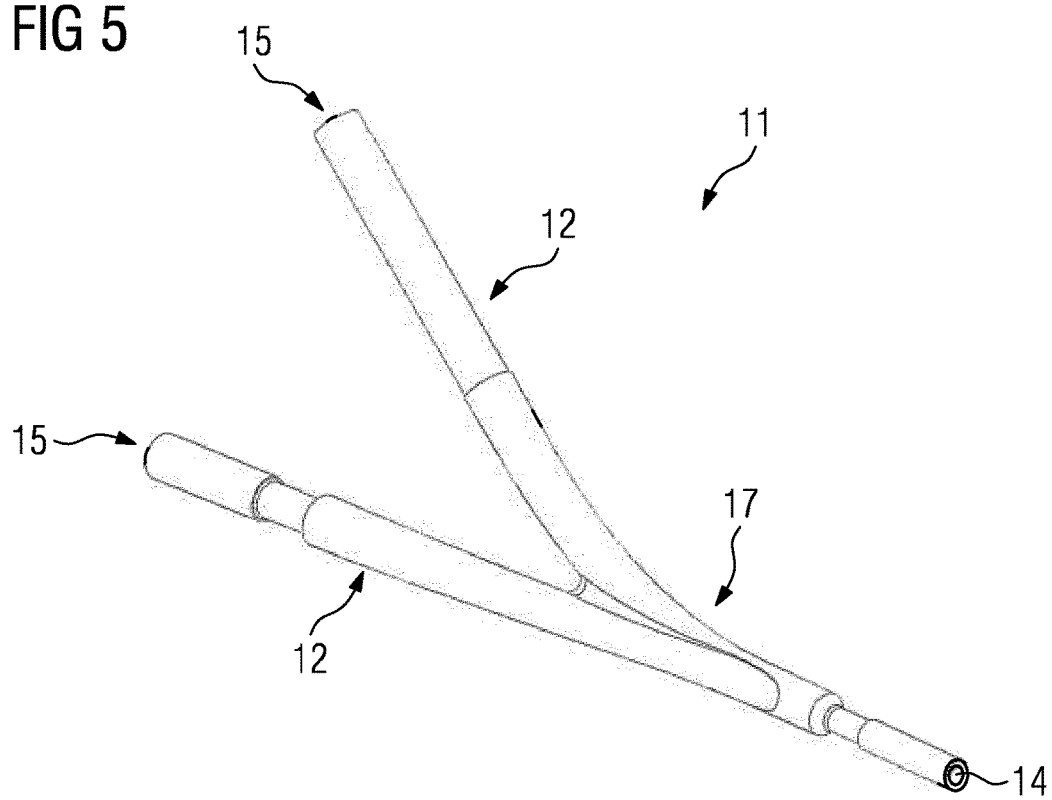
Figure 6:
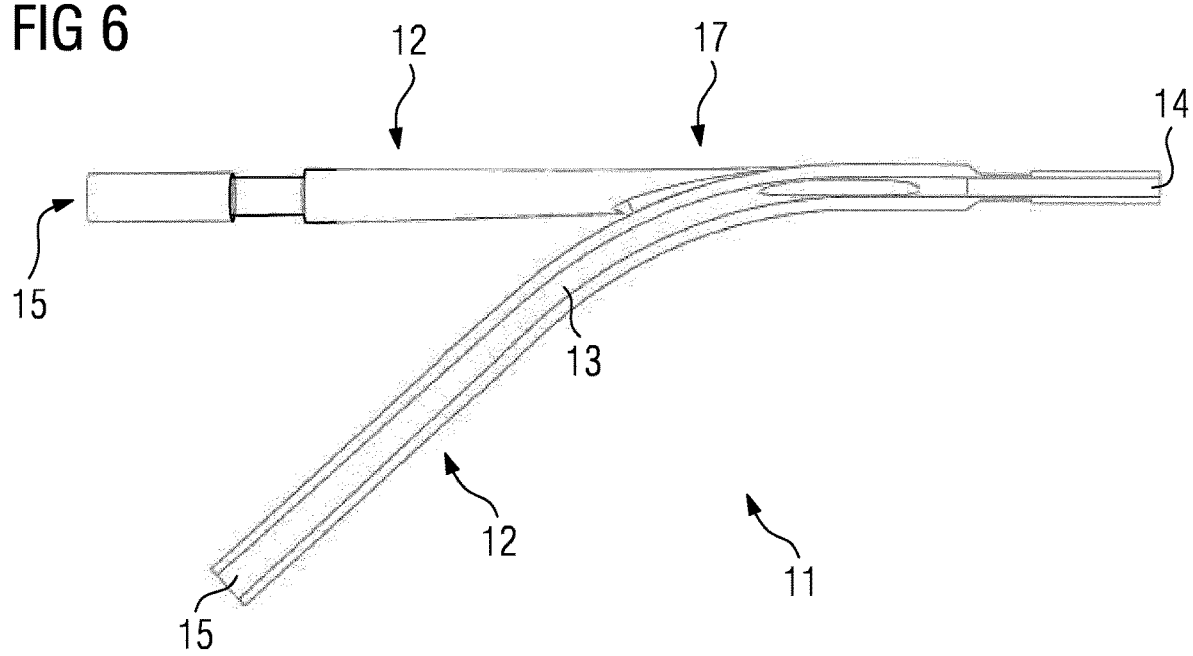
Figure 7:
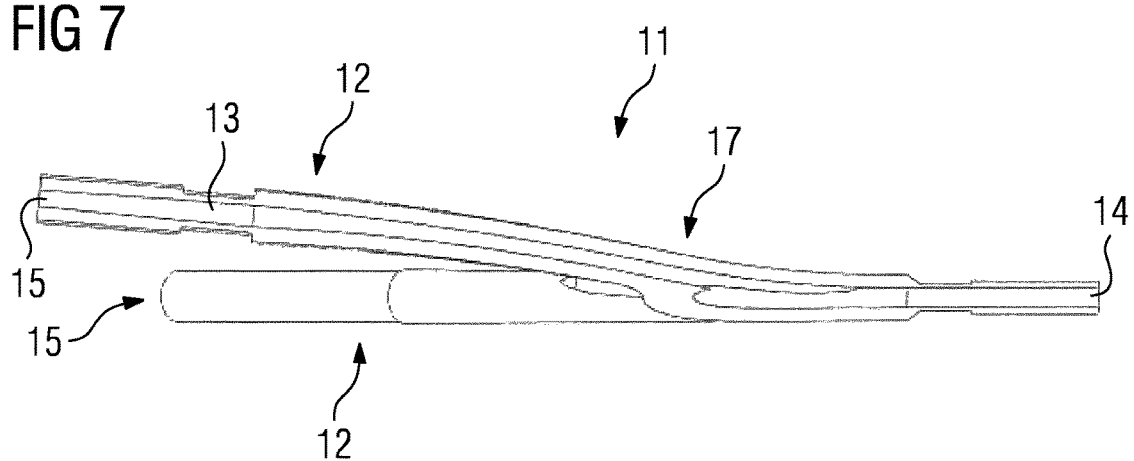

On the basis of the exemplary embodiment shown in FIGS. 5 through 7, in which a perspective view (cf. FIG. 5) and two partially longitudinally cut views (cf. FIGS. 6, 7) of a component 11 are represented, it is apparent that a channel 13 can be designed, in an area located between two free ends of the component 11, comprising a Y-like or -shaped junction 17 at which a channel 13 branches into a further channel 13 (side channel). In this way as well, the component 11 comprises a different number of channels 13 along its longitudinal extension; the number of channels 13 upstream and downstream from such a junction 17 can therefore vary due to the branching of the channel 13 into at least two channels 13.

On the basis of the exemplary embodiments shown in FIGS. 2 through 9, it is apparent, in general, that a component-side channel structure 12 can comprise multiple channels 13. The channel structure 12 can be designed comprising multiple channels 13 communicating with one another, in particular at appropriate branch points 16 or junctions 17.

Figure 8:
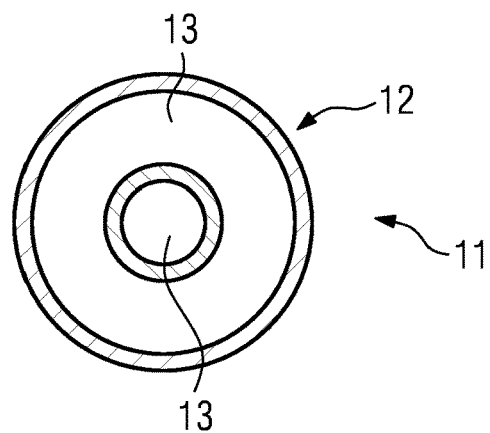
Figure 9:
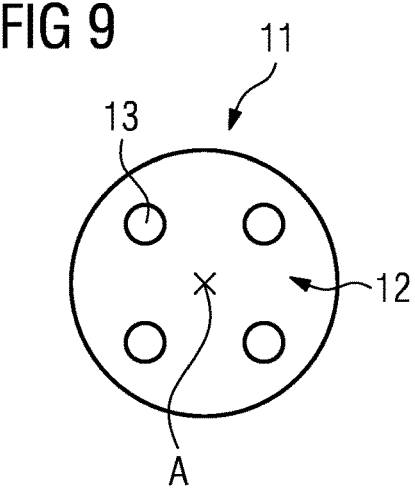

On the basis of the exemplary embodiments shown in FIGS. 8 and 9, in which a component 11 is represented in a transversely cut view, it is apparent that a channel structure 12 can also be designed comprising multiple channels 13 that are not communicating with one another.

In the exemplary embodiment shown in FIG. 8, the channels 13 are designed to be coaxially arranged. The channel structure 12, viewed in cross section, comprises multiple channels 13 extending coaxially, i.e., within one another. A first or inner channel 13 having a first outer diameter extends within a second or outer channel 13 having a larger second outer diameter. In this way, it is possible to implement different functionalities of the channel structure 12 across the overall cross section of the component 11; for example, a medical functional element, i.e., for example, a medical instrument, can be passed through the inner channel 13, and a medium can be passed through an outer channel 13 enclosing the inner channel 13, or vice versa. It is also conceivable to pass different media, if necessary having different flow parameters, or different functional elements through different channels 13. In particular, it is conceivable to utilize a first channel 13 as a supply channel for supplying a medium and to utilize a second channel 13 as a drainage channel for draining a medium.

In the exemplary embodiment shown in FIG. 9, multiple channels 13 are arranged spaced apart or adjacent to one another, circumferentially about a central axis A of the component 11. In this way as well, it is possible to implement different functionalities of the channel structure 12 across the overall cross section of the component 11; for example, a medical functional element, i.e., for example, a medical instrument, can be passed through a first channel 13, and a medium can be passed through a second channel 13 arranged circumferentially adjacent to the first channel 13. It is also conceivable in this case, of course, to pass different media, having different flow parameters, if necessary, or different functional elements through different channels 13.

Within the scope of the method, i.e., in particular after completion of the additive construction process of the component 11, at least one measure can be carried out for mechanically processing the walls of the component 13, or its surface, delimiting a particular channel 12. Due to an appropriate mechanical processing or reworking, the structural properties, in particular of the surfaces, of the walls delimiting the particular channel 13 can be affected in a targeted manner in order to affect, for example, the flow behavior of a medium flowing through the particular channel, for example, by forming a certain surface structure or a certain surface roughness.

As a measure for mechanically processing, at least in segments, the wall thickness of the walls delimiting a particular channel 13, a fluid flow, which contains, in particular abrasive, particles removing material from the walls delimiting the at least one channel 13, can be passed through a particular channel 13. By passing a fluid flow containing material-removing particles through the channel 13, the wall thickness of the walls can be reduced to a desired dimension or the channel cross section can be increased to a desired dimension. For example, hard mineral particles (or mixtures thereof), i.e., in particular, corundum particles (or mixtures thereof), can be utilized as material-removing particles. The fluid flow is a gas or liquid flow, which flows through the particular channel 13 at a flow rate that is sufficiently high for removing material from the walls.

As a measure for mechanically processing, at least in segments, the surface of the walls delimiting the particular channel 13, a fluid flow, which contains particles smoothing the surface of the walls delimiting the at least one channel 13, can be passed through a particular channel 13. By passing a fluid flow containing smoothing particles through the channel 13, the surface of the walls can be formed having a desired roughness. For example, hard glass or silicon oxide particles (or mixtures thereof), i.e., in particular, glass bead particles (or mixtures thereof), can be utilized as smoothing particles. The fluid flow, in turn, is a gas or liquid flow, which flows through the particular channel 13 at a flow rate that is sufficiently high for smoothing the surface with the aid of the particles. After an appropriate smoothing, the surface of the walls delimiting the particular channel 13 can have, for example, a surface roughness Ra below 0.9, in particular below 0.8.

A particular fluid flow is typically directed from channel sections or channels 13 having a comparatively larger cross-sectional area in the direction of channel sections or channels 13 having a comparatively smaller cross-sectional area. The angle of entry of the particular fluid flow is in a range typically between 0° and 90° in relation to the central axis A of the particular channel 13, depending on the course of the particular channel 13. Particularly positive material-removal and smoothing results can be achieved in this way.

The component 11 can be designed comprising an introduction section (not shown) including an introduction opening for introducing the fluid flow containing particular particles into the particular channel 13. The introduction, in particular of the particles, can therefore take place via an introduction section designed specifically for this purpose.

The introduction section can form an inherent part of the component 11, but it can be removed after the at least one measure for mechanically processing, at least in segments, the walls delimiting the at least one channel 13 has been carried out. Upon an introduction (injection) of the fluid flow containing appropriate particles, the introduction axis of the fluid flow can extend, with respect to the tangent to the central axis A, in the direction of an inner radius of the first change in direction or bend in the course of the channel 13.

In all exemplary embodiments, at least one handling element (not shown), in particular a handle element for a user, or a tool element, in particular a grasping element, for example, for grasping tissue of an object, can be arranged or formed or can have been arranged or formed on the component 11, in particular in the area of a free end. The handling element or the tool element can be detachably (without causing damage or destruction) or non-detachably fastened on the component 11 as a separate component group. It is also conceivable, of course, to additively manufacture the handling element or the tool element, i.e., to form it as an inherent part of the component 11, in particular within the scope of the additive manufacturing of the component 11.

Moreover, in all exemplary embodiments, the component 11 can be designed comprising an extension and/or compression structure (not shown) enabling an extension or compression, in segments, of the component 11 in the longitudinal direction of the component 11. Therefore, the component 11 can be extended or compressed, in segments, in a targeted manner, which improves, for example, its handling, in particular within an object. Appropriate extension and/or compression structures can have, for example, a bellows-like or—shaped geometric-structural shape, which can be readily formed within the scope of the additive manufacturing of the component 11.

Moreover, in all exemplary embodiments, the component 11 can be designed comprising at least one permeation structure (not shown) enabling a permeation, in segments, of a medium out of a channel 13 into the surroundings around the component 11. Therefore, the component 11 can be utilized for a targeted release of a medium, i.e., for example, a medically active substance, via an appropriate permeation structure, which can be formed, for example, by permeation areas or openings, which are "passable" by a medium.

Finally, in all exemplary embodiments, a particular channel 13 or a channel section forming a component of a particular channel 13 can be designed having an inner diameter of the channel in a range between 0.25 mm and 3 mm, in particular in a range between 0.5 mm and 2.5 mm. The wall thickness of the walls delimiting a particular channel 13 can also be in a range between 0.25 mm and 3 mm, in particular in a range between 0.5 mm and 2.5 mm. It is possible, of course, that the walls delimiting a particular channel 13 have different inner diameters or different wall thicknesses along the longitudinal extension of the channel 13.

The invention claimed is:

1. A method of manufacturing a medical component, the method comprising:
   additively manufacturing, via powder based additive manufacturing, a medical component at least in part by successive, layer-by-layer, selective exposure and associated successive, layer-by-layer, selective solidification of construction material layers made of a powdered construction material solidifiable with an energy beam;
   wherein the medical component is insertable at least partially into a body of a living being, and wherein the medical component comprises a channel structure having one or more walls that define one or more channels, the one or more channels having a tubular configuration through which a medium and/or at least one functional element can be passed; and smoothening a surface of the one or more walls at least in part by a fluid comprising abrasive particles flowing through the at least a portion of the one or more channels defined by the one or more walls;

wherein the channel structure comprises at least one branch point at which a respective one of the one or more channels branches into at least two channels;

wherein the one or more channels have a cross-sectional area that varies along a central axis of the one or more channels from a comparatively lager cross-sectional area to a comparatively smaller cross-sectional area;

wherein flowing the fluid through at least a portion of the one or more channels comprises flowing the fluid in a direction from the comparatively larger cross-sectional area to the comparatively smaller cross-sectional area; and wherein the medical component is an endoscope.

2. The method of claim 1, comprising:
mechanically processing at least a portion of the one or more walls of the channel structure.

3. The method of claim 1, wherein at least a portion of respective ones of the one or more channels extends in a linear manner and/or in a curved manner.

4. The method of claim 1, wherein the channel structure comprises at least one junction at which a respective one of the one or more channels branches into at least one further channel.

5. The method of claim 1, wherein the medical component comprises
at least one handling element arranged or formed at a first free end of the medical component; and/or
wherein the medical component comprises a grasping element arranged or formed at a second free end of the medical component, wherein the grasping element is configured for grasping tissue of an object.

6. The method of claim 1, wherein at least a portion of the one or more channels has an inner diameter of from 0.25 mm to 3 mm.

7. The method of claim 1, wherein the medical component comprises
at least one extension structure configured to cause extension of the medical component in a longitudinal direction; and/or
wherein the medical component comprises at least one compression structure configured to cause compression of the medical component in the longitudinal direction.

8. The method of claim 1, wherein the one or more channels comprises a permeation structure having openings configured to pass a medium from the one or more channels into a targeted portion of the body of the living being.

9. The method of claim 1, wherein the fluid comprises a gas.

10. The method of claim 1, wherein the abrasive particles comprise hard mineral particles.

11. The method of claim 10, wherein the hard mineral particles comprise corundum particles.

12. The method of claim 1, wherein the one or more channels comprises a plurality of channels communicating with one another at corresponding branch points or junctions.

13. The method of claim 12, wherein the one or more channels comprises a first channel and a second channel that are coaxially arranged relative to one another.

14. The method of claim 12, wherein the one or more channels comprises a plurality of channels that are arranged adjacent to one another and circumferentially about a central axis of the medical component.

15. The method of claim 12, wherein the medical component comprises an introduction section that has an introduction opening for introducing the fluid into the at least a portion of the one or more channels.

16. A method of manufacturing a medical component, the method comprising:
additively manufacturing, via powder based additive manufacturing, a medical component at least in part by successive, layer-by-layer, selective exposure and associated successive, layer-by-layer, selective solidification of construction material layers made of a powdered construction material solidifiable with an energy beam;
wherein the medical component is insertable at least partially into a body of a living being,
wherein the medical component comprises a channel structure having one or more walls that define one or more channels and comprises at least one branch point at which a respective one of the one or more channels branches into at least two channels, the at least two channels having a tubular configuration through which a medium and/or at least one functional element can be passed;
wherein the medical component is an endoscope; and
removing material from the one or more walls of the at least two channels at least in part by a fluid comprising abrasive particles flowing through the at least two channels.

17. The method of claim 16, wherein the at least two channels comprises a first channel and a second channel that are coaxially arranged relative to one another.

18. The method of claim 16, wherein the at least two channels comprises a plurality of channels that are arranged adjacent to one another and circumferentially about a central axis of the medical component.

19. The method of claim 16, wherein the one or more channels have a cross-sectional area that varies along a central axis of the one or more channels from a comparatively lager cross-sectional area to a comparatively smaller cross-sectional area.

* * * * *